United States Patent [19]

Hargis et al.

[11] 4,020,115
[45] Apr. 26, 1977

[54] ALKALINE BARIUM ALCOHOLATES

[75] Inventors: Ivan Glen Hargis, Tallmadge; Russell Anthony Livigni; Sundar Lal Aggarwal, both of Akron, all of Ohio

[73] Assignee: The General Tire & Rubber Company, Akron, Ohio

[22] Filed: Apr. 23, 1976

[21] Appl. No.: 679,542

Related U.S. Application Data

[62] Division of Ser. No. 593,579, July 7, 1975, Pat. No. 3,992,561.

[52] U.S. Cl. .................. 260/632 A; 260/617 R
[51] Int. Cl.$^2$ .............. C07C 29/00; C07C 31/30; C07C 35/21
[58] Field of Search .............. 260/632 A, 617 R

[56] References Cited

UNITED STATES PATENTS

| | | | |
|---|---|---|---|
| 3,009,964 | 11/1961 | Russell | 260/632 A |
| 3,094,546 | 6/1963 | Towers | 260/632 A |
| 3,100,750 | 8/1963 | Bailey et al. | 260/632 A |
| 3,210,404 | 10/1965 | Durr et al. | 260/632 A |
| 3,971,833 | 7/1976 | Lenz et al. | 260/632 A |

OTHER PUBLICATIONS

Turova et al, "Russian Chemical Reviews", vol. 34 (Mar. 1965), pp. 161–185.

*Primary Examiner*—Joseph E. Evans

[57] ABSTRACT

This invention relates to the preparation of solution polymers and rubbers from vinyl monomers using a new catalyst complex of a barium di-tert-alkoxide-hydroxide salt and an organic lithium compound. In particular, homopolymers and copolymers of butadiene with styrene and/or isoprene, prepared with this catalyst, are uniquely characterized by the butadiene units having a low vinyl content (not over about 12%) and a trans-1,4 structure of from about 70 to 81%. Also, the copolymer has a random comonomer sequence distribution. This molecular structure permits elastomers containing little or no styrene to have sufficient stereoregularity to crystallize. Furthermore, the butadiene homopolymer and copolymer with styrene and/or isoprene exhibit a broad molecular weight distribution as well as tack and green-strength which are valuable properties for a rubber to possess when building tires.

10 Claims, 4 Drawing Figures

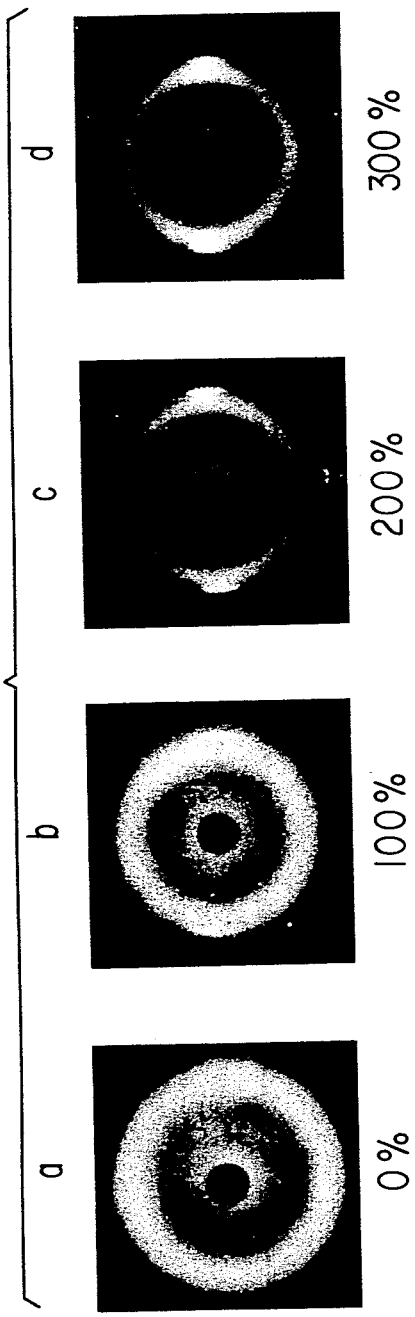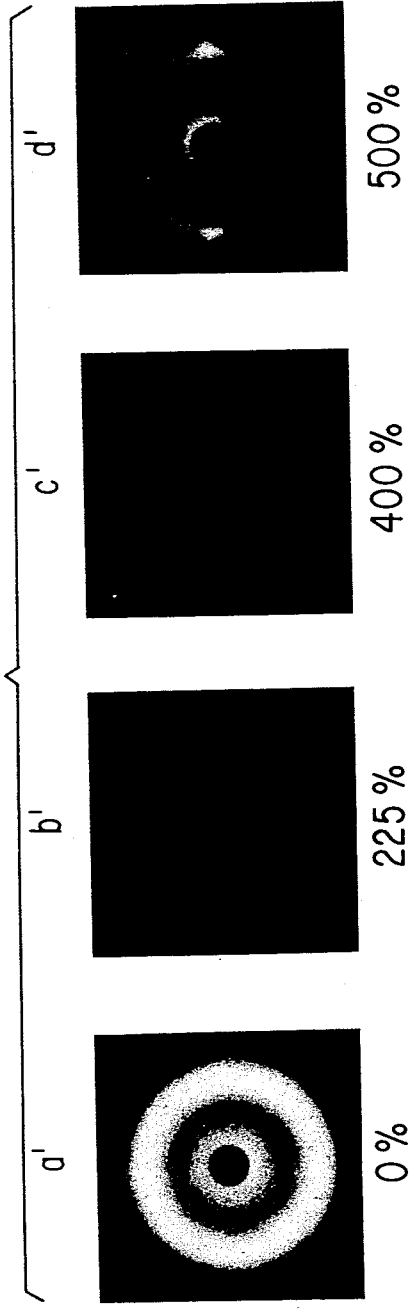

ALKALINE BARIUM ALCOHOLATES

This application is a division of prior copending U.S. patent application Ser. No. 593,579 filed July 7, 1975, now U.S. Pat. No. 3,992,561, patented Nov. 16, 1976.

DISCUSSION OF THE PRIOR ART

It is known that copolymers of the conjugated diene monomers (butadiene-1,3 and isoprene) with styrene, which are prepared using alkyllithiums in hydrocarbon solvents, have a graded block-type structure [Kelley, D. J. and Tobolsky, A. V., "J. Am. Chem. Soc., "81, 1597 (1959) and Kuntz, I., "J. Polym. Sci.,"54, 569 (1961)]. For a copolymerization using an equal molar mixture of butadiene and styrene, butadiene is consumed initially much more rapidly than the styrene. When the butadiene concentration drops to a small value, the styrene is then rapidly consumed. Since this type of polymerization is nonterminating, the styrene is added to the same polymer chain which already contains a segment essentially of butadiene units forming a graded block copolymer having a trans content for the butadiene segment of about 53%. If a polar compound such as tetrahydrofuran, diethyl ether, or the like, is added to this copolymerization process, the reactivity of the styrene is increased during the initial stage of the reaction and copolymers having a more random structure result. However, this technique of preparing random copolymers has the disadvantage of increasing the vinyl content of the butadiene segments from 6–10% to as high as 70% or more, dependent on the nature of the polar compound used to prepare the random copolymers, and of reducing the trans content below 55% depending on the amount of polar compound employed. Rubbers possessing a relatively high vinyl content from the butadiene are undesirable in certain tire applications where the tire must have good dynamic response. Various techniques have been described which circumvent the formation of polybutadienes containing high vinyl contents while still permitting the preparation of random copolymers of butadiene with comonomers such as styrene. One of these methods involves the addition of the comonomers at a certain rate to the reaction system during copolymerization to provide a copolymer in which the butadiene segments have a microstructure of 5–15% vinyl and 30–60% cis or trans units [U.S. Pat. No. 3,094,512]. Another technique is to add incrementally butadiene (the most reactive monomer) at a rate to maintain a high styrene/butadiene ratio during polymerization to provide a copolymer where the butadiene units exhibit at least 30% cis, not over 46.4% trans and not over 12% vinyl [British Pat. No. 994,726 (1965)]. A method which does not require any programmed addition of monomer is based on the use of polymerization temperatures from 93° to over 154° C. [U.S. Pat. No. 3,558,575]; the method provides SBR polymers having 49.1 – 52.7% trans, 9.9 – 10.6% vinyl and a HI of 2.65. Organometallic compounds of Cs, Rb, K or Na as well as their salts of alcohols, phenols, carboxylic acids, carbonates, their sulfur analogs and amines have been used with organolithiums in the preparation of random copolymers having for the butadiene segments a vinyl content of 8.8 to 26.9% and trans content of 45.8 to 58.2% (U.S. Pat. No. 3,294,768). The addition to such systems of polar compounds per se, such as oxygen, water, alcohols, primary amines and secondary amines in an alkyl substituted aromatic diluent will provide liquid, random copolymers (U.S. Pat. No. 3,324,191) and can result in a reduction in the amount of organolithium compound used. Alkali metal t-butoxides with the exception of lithium t-butoxide have been found to be effective in accelerating the rate of copolymerization at which styrene is incorporated and increasing the overall rate of copolymerization. For the butyllithium initiated copolymerization of butadiene with styrene carried out in the presence of lithium t-butoxide a block polymer is obtained with a negligible change in the styrene incorporated with conversion [Wofford, C.F., and Hsieh, H.L., "J. Polymer Sci,," 7, Part A-1, 461 (1969)]. U.S. Pat. No. 3,506,631 teaches that aliphatic or aromatic phosphites, thiophosphites or amidophosphites in combination with n-butyllithium provide a random copolymer with vinyl contets of 10.7–15.3%. Patent application No. 69/14,452 (Netherlands) clams an improved process for the copolymerization of butadiene with styrene using a catalyst comprised of an alkali metal oxide, hydroxide, superoxide or peroxide with an organolithium compound. The resulting copolymers have a random styrene placement with a microstructure of 52.4–55.6% trans and 11.0–11.6% vinyl. The alkali metals, sodium and potassium, have been reacted with organolithiums to provide catalysts for the preparation of random solution butadiene-styrene copolymerss having vinyl contents of 7.3–25% and trans contents of 37.1–59.1% (Patent Application No. 48,069 (1968) Australia). A catalyst system for diene polymerization using an organolithium in combination with a barium compound including barium stearate and barium t-butoxide is stated to provide random copolymers of certain dienes and mono-vinyl aromatic compounds, not described as being crystalline, having a vinyl content of 7.8–13% and a trans content using Ba t-butoxide as high as 67.9% and using barium stearate of 70.5% (Examples 1 and 13, U.S. Pat. No. 3,629,213 (1971), Akira Onishi, Ryota Fujio, Minoru Kojima and Hiroschi Kawamoto, assignors to Bridgestone Tire Company Limited). Ryota Fujio, Minoru Kojima, Shiro Anzai and Akira Onishi (Bridgestone Tire Co., Ltd.), "Kogyl Kagaku Zasshi," No. 2 (19729, pages 447–453, in a somewhat similar disclosure show the reaction of alkaline earth metals directly with active hydrogen containing compounds (apparently in benzene), the use of barium stearate with an organolithium to provide 52.5% trans for a butadiene-styrene copolymer, state that barium stearate is scarcely effective and show limited molecular weight distributions, but do not show any crystallinity for their polymers.

White, tough, thermoplastic homopolybutadienes having 92 to 100% trans,-1,4 units and useful for making floor tile, golf ball covers and battery cases can be obtained by the polymerization of butadiene in hydrocarbon solvent using a catalyst mixture of an alkylaluminum dihalide and a beta-diketone complex of V, Fe or Ti as disclosed in U.S. Pat. No. 3,268,500. A blend of amorphous and crystalline homopolybutadienes in which the crystalline fractions contain 90 to 99% trans-1,4 structures are obtained by polymerizing butadiene with a mixed catalyst of $TiCl_3$, $VCl_3$ or $VOCl_3$ and Al alkyls, Zn alkyls, or dialkyl Al halides according to U.S. Pat. No. 3,550,158. Neither one of these patents disclose copolymers of styrene. A mixture of allyl potassium and potassium allyloxide in an aliphatic diluent is used to polymerize butadiene to obtain a mixed homopolymerizate containing overall about 64% trans-1,4 configuration as disclosed by U.S. Pat. No.

3,607,851. While this patent states that styrene can be included, an actual copolymerization is not shown. Polybutadienes having trans-1,4 contents of 68–79.6% and vinyl contents of 8–20% and a butadiene-styrene block copolymer having a trans-1,4 content of 68% and a vinyl content of 8% are disclosed as being prepared in cyclohexane or toluene using an organocalcium polymerization initiator made by contacting calcium metal with a polynuclear aromatic or a polyaryl substituted ethylene compound in a polyether diluent in the presence of a promoter such as 1,2-dibromoethane to expose fresh calcium surface metal (U.S. Pat. No. 3,642,922). It, also, discloses that organo-lithium catalyzed copolymers of butadiene and styrene have trans-1,4 contents of 46% and vinyl contents of 33%. Low molecular weight homopolymers or block, tapered block or random copolymers of dienes or dienes plus 5.1–42.2% styrene having trans-1,4 contents of from 59.8 to 77.2% and vinyl contents of 6.9–13.5% are prepared in hydrocarbon solvents at −30° to 160° C. using as a catalyst an Ate-compound of the formula $M^1M^2R^1R^3R^4$ where $M^1$ is Ca, Ba or Sr and $M^2$ is Zn or Cd and the Rs are hydrocarbons (U.S. Pat. No. 3,665,062); the polymers thereby obtained are not shown to be crystalline. Polybutadienes having trans-1,4 contents of from 8.17 to 86.7% and vinyl contents of from 6.7 to 9.2% are obtained by polymerizing the diene in hydrocarbon diluent at −100° to 200° F. using as a catalyst a mixture of an organocalcium compound and an organoaluminum compounds, e.g., calcium anthracene reaction product and triisobutylaluminum (U.S. Pat. No. 3,687,916). While it states that mixtures of monomers can be polymerized, it does not show any copolymers. Copolymers of 58–52% styrene and 42–48% butadiene exhibiting 80–84% trans-1,4 and 6% vinyl units were prepared from their mixtures in cyclohexane using as a catalyst an organometallic compound of Ca, Ba or Sr such as a solution of bis (benzyl) calcium in tetrahydrofuran according to U.S. Pat. No. 3,718,703. Homopolymers of butadiene and random copolymers of butadiene and up to about 25% styrene, exhibiting crystallinity when stretched and having trans-1,4 contents of 66.7 to 86%, vinyl contents of 6.1 to 9.4% and a $\overline{M}_w/\overline{M}_n$ (heterogeneity index) of 1.38–2.19, using various ratios of a barium di-tert alkoxide and a dibutyl magnesium compound are disclosed in U.S. Pat. No. 3,846,385. Alfin rubbers from butadiene and styrene using as a catalyst a mixture of sodium allyl, sodium alkoxide and sodium chloride are said to be crystalline having a trans-1,4 content of 70% and a high vinyl content of 30% (T. Sato, "Rubber Age," January, 1970, pages 64 to 71). According to U.S. Pat. No. 3,464,961 increasing the amount of styrene in the copolymer reduces crystallinity while according to U.S. Pat. No. 3,759,919 increasing the amount of styrene incorporated in the copolymer does not apparently affect the trans content.

OBJECTS

An object of this invention is to provide a novel barium alkoxide-hydroxide compound useful in making a catalyst and method for making the same.

Another object of this invention is to provide a novel catalyst complex of barium alkoxide-hydroxide and an organolithium useful for the anionic polymerization and copolymerization in solvent of certain ethylenically unsaturated monomers.

A further object of this invention is to provide a novel process for the anionic solution polymerization and copolymerization of certain ethylenically unsaturated monomers utilizing a catalyst complex of a certain barium alkoxide-hydroxide compound and an organo lithium compound.

A still further object is to provide a homopolymer of butadiene-1,3 or a random copolymer of butadiene-1,3 and up to about a total of 15% of the weight of said copolymer of copolymerized isoprene and/or styrene, said copolymer exhibiting crystallinity on stretching uncompounded and uncured, a low vinyl content and at least 70% trans-1,4 content.

These and other objects and advantages of the present invention will become more apparent to those skilled in the art from the following detailed description, examples and accompanying drawings in which:

FIG. 3 shows x-ray diffraction photographs of high trans polybutadienes of this invention at various percent elongations; and FIG. 4 shows x-ray diffraction photographs of high trans butadiene-styrene copolymers containing 5% styrene of this invention at various elongations.

SUMMARY OF THE INVENTION

Figure 1:
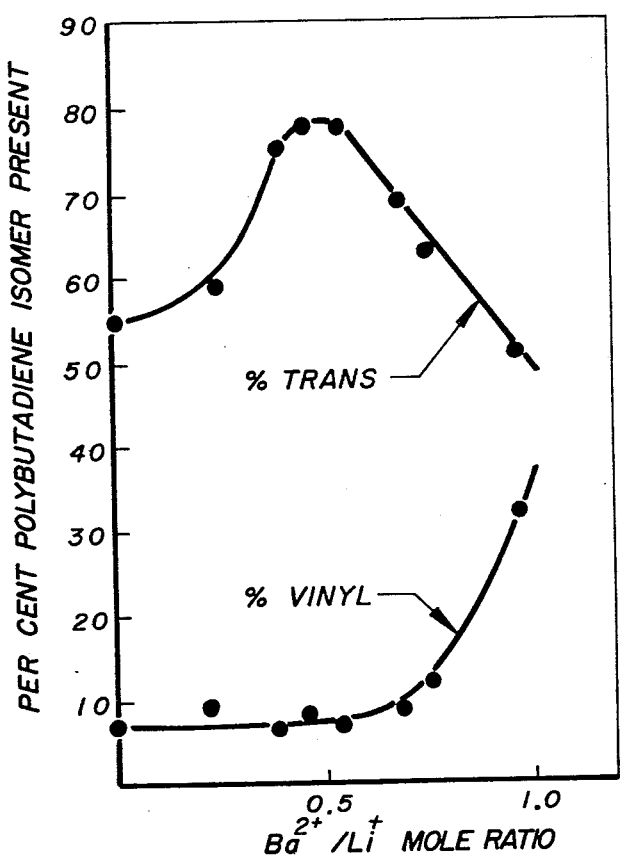
FIG. 1 is a graph showing the dependence of the polybutadiene microstructure (of the butadiene units in a rubbery butadiene polymer prepared according to the present invention) on the composition (mole ratio) of the barium alkoxy-hydroxy compound to the organo lithium compound in the catalyst complex.

It has been found that a polymerizable vinyl monomer having an activated double bond, having up to 14 carbon atoms, and being free of groups which would destroy the catalyst complex, can be polymerized under inert conditions in a hydrocarbon solvent at a temperature of from about −90° to 100° C. using as a catalyst, in a minor effective amount sufficient to polymerize said monomer, a complex of

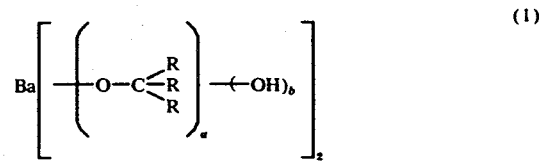

where at least one R is a methyl or cyclohexyl radical and where the remaining R's are selected from the group consisting of alkyl and cycloalkyl radicals having from 1 to 6 carbon atoms which may be the same or different and where the mol ratio of a to b is from about 99.5:0.5 to 88:12 and (2) R'Li in which R' is selected from the group consisting of normal, secondary and tertiary alkyl and cycloalkyl radicals having from 2 to 20 carbon atoms, the mol ratio of (1) to (2) based on barium metal and lithium metal being from about 0.30:1 to 0.75:1, said solvent being a solvent for said monomer and polymer.

The catalyst complex of the invention is particularly useful in making rubbery butadiene-1,3 homopolymers and copolymers of butadiene-1,3 and up to about 15% by weight of copolymerized styrene and/or isoprene.

These butadiene polymers undergo stress induced crystallization at room temperature so that they can adhere during fabrication of rubber articles: for example, they have building tack and do not necessarily need a separate added tackifier to provide tack.

These butadiene polymers, also, exhibit green-strength which is related to their crystallinity on elongation at room temperature and also to their molecular weight distribution. The copolymers, also, are essentially amorphous at room temperature in the unstretched state which is desirable for a tire rubber. The fact that these rubbers crystallize and have good green strength also makes them useful as contact adhesives.

In particular, rubbery homopolybutadiene and rubbery random copolymers of butadiene-1,3 and up to about 15% by weight total of said copolymer of copolymerized styrene and/or isoprene prepared according to the present invention exhibit:

a. a glass transition temperature of from about $-80°$ to $-100°$ C. as determined by differential thermal analysis, b. a crystalline melting point (peak values) in the unstretched state of from about $-10°$ to $+43+$ C. as determined by differential thermal analysis, c. a trans-1,4 content of from about 70 to 81% and a vinyl content of up to about 12% for the butadiene units, d. a heterogeneity index of from about 4 to 40, e. a number average molecular weight of from about 20,000 to 300,000, f. crystallinity when stretched in the uncompounded and uncured state as shown by x-ray diffraction data and g. green strength and building tack.

DISCUSSION OF DETAILS AND PREFERRED EMBODIMENTS

The barium tertiary alkoxide-hydroxide salt is obtained by reacting barium metal, preferably in finely divided form and in a stoichiometric amount, with a tertiary carbinol and water in liquid $NH_3$ or amine solvent for the barium at a temperature of from about $-100°$ C. up to the boiling point of the solvent. Examples of tertiary carbinols which may be used are tertiary butanol, 3-methyl-3-pentanol, 2-methyl-2-butanol, 2-methyl-2-pentanol, 3-methyl-3-hexanol, 3,7-dimethyl-3-octanol, 2-methyl-2-heptanol, 3-methyl-3-heptanol, 2,4-dimethyl-2-pentanol, 2,4,4-trimethyl-2-pentanol, 2-methyl-2-octanol, tricyclohexyl carbinol, dicyclopropyl methyl carbinol, dicyclohexylpropyl carbinol and cyclohexyl dimethyl carbinol, and the like and mixtures thereof. These tertiary carbinols have the formula

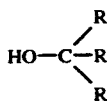

where at least one of the Rs is a methyl or cyclohexyl radical and the remaining Rs are selected from the group consisting of alkyl or cycloalkyl radicals of from 1 to 6 carbon atoms which may be the same or different such as a methyl, ethyl, propyl, isopropyl, amyl, cyclohexyl, and the like radical. Preferably in the tertiary carbinol used, the Rs are all methyl groups.

The amount of water in the water and tertiary carbinol mixture varies from about 0.5 to 12, preferably from about 2.5 to 10, mol % of the mixture.

The solvent used in preparing the barium alkoxide-hydroxide component or moiety of the catalyst is selected from the group consisting of liquid $NH_3$ and saturated non-polymerizable non-chelating aliphatic, cycloaliphatic and heterocyclic, primary and secondary, mono amines and poly-amines and mixtures thereof, having from 1 to 12 carbon atoms and from 1 to 3 nitrogen atoms and being a liquid at a temperature of from about $-100°$ C up to the boiling point of the solvent and at a pressure of from about 0.25 to 10 atmospheres. Examples of such amines are methylamine, dimethylamine, ethylamine, n-propylamine, n-butylamine, n-amylamine, n-hexylamine, ethylene diamine, pentamethylene-diamine, hexamethylenediamine, din-propylamine, diisopropylamine, diethylamine, cyclohexylamine, N-butyl cyclohexylamine, N-ethylcyclohexylamine, N-methyl cyclohexylamine, diethylene triamine, cyclopentylamine, diamylamine, dibutylamine, diisoamyl amine, diisobutylamine, dicyclohexylamine, piperidine, pyrrolidine, butyl ethylamine, and the like and mixtures thereof. Lower molecular weight amines are preferred since less is required to solvate the metal. It is preferred that the $NH_3$ or amine be pure. However, commercially available materials can be used provided that they do not contain more than about 2% by weight of by-products or impurities such as triamines, other alcohols and water which will have to be considered when preparing the barium salt. Any material which would adversely affect the effectiveness of the barium salt as a catalyst component should be removed from the $NH_3$ or amine. The amine should be a solvent for the barium or at least dissolve it in part so that it can react with the tertiary carbinol and $H_2O$ mixture.

In preparing the barium tertiary alkoxide-hydroxide salt, sufficient $NH_3$ or amine solvent is employed to dissolve the metal. Preferably, an excess of the amine or $NH_3$ is employed. When preparing catalysts at low temperatures, it is not necessary to use pressure equipment. However, pressure equipment can be employed, and the process of preparing the catalyst can occur at pressures of from about 0.25 to 10 atmospheres dependent on the vapor pressure of the amine solvent used. During preparation of the catalyst it is desirable to agitate the reaction mixture during addition and reaction of the reagents. Further, it is preferred that an inert atmosphere, for example, helium, neon, or argon is maintained over the reaction mixture at all times to prevent contact of the product with air. Of course, in place of the inert gas, the vapor of the organic compound and/or amine can be used as the "inert atmosphere." Closed reactors should be employed. It is not desirable to prepare the barium di-tert-alkoxide-hydroxide in bulk or in benzene since the reaction is slow and not as quantitative and since benzene or its residues can interfer with subsequent polymerization.

After preparation of the barium salt, the amine or $NH_3$ is separated by distillation, vacuum evaporation, solvent extraction and so forth utilizing temperatures, pressures and solvents which do not adversely affect the barium salt. The amine or $NH_3$ may simply be evaporated from the salt, any excess carbinol removed, and the salt, dried in vacuum for example at about 50° C., dissolved in one or more aromatic hydrocarbon solvents such as benzene, toluene or the like. Since the amount of barium salt solution is so small in relation to the other materials, the aromatic hydrocarbon solvent used for the salt does not necessarily have to be, but is preferred to be, the same as that used for the polymerization solvent. Dilute solutions of the barium salt in the aromatic hydrocarbon solvents are generally preferred for injection into the polymerization reactor.

The yield of the barium salt based on the weight increase of the barium can be from about 95 to 100%. The solution of the barium salt in the aromatic solvent may be used as prepared. However, it is usually allowed to stand overnight to allow a precipitate to settle out. About 30 to 85% by weight of the barium salt as an active catalyst component is in the solution phase. The solution phase can be separated from the solid phase by decantation, filtration or centrifugation. While the solid phase or precipitate is not useful as a catalyst component, it can be mixed or dispersed with the solution phase and used in polymerization. It will be appreciated that barium is insoluble in benzene, barium hydroxide is insoluble in benzene and toluene and barium di (tertiary butoxide), for example, is sparingly soluble in benzene.

The resulting barium salt has the following general formula:

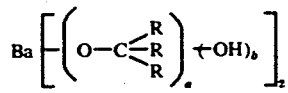

where the mol ratio of $a$ to $b$ is from a bout 99.5:0.5 to 88:12, preferably from about 97.5: 2.5 to 90:10, and where the Rs are as defined above. Preferably the Rs are methyl radicals. Mixtures of the barium salts can be used in the practice of the present invention.

Other ways to describe the barium salts are as follows:

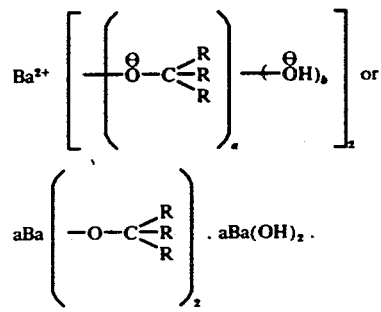

The barium tertiary alkoxide-hydroxide salt of this invention is not an effective catalyst by itself for the polymerization of butadiene or mixtures of butadiene plus styrene and/or isoprene but in combination with the organolithium component it provides rubbéry high trans, high molecular weight polymers.

The organolithium compound used in the present invention has the following general formula:

R'Li wherein R' represents a normal, secondary or tertiary alkyl and cycloalkyl radical having from 2 to 20 carbon atoms. Examples of the organo-lithium compounds are ethyllithium, n-propllithium, isopropyllithium, n-butyllithium, isobutyllithium, sec-butyllithium, tert-butyllithium, n-amyllithium, isoamyllithium, n-hexyllithium, 2-ethylhexyllithium, n-octyllithium, n-decyllithium, cyclopentyllithium, cyclohexyllithium, methylcyclohexyllithium, cyclohexylethyllithium, and the like and mixtures thereof. Preferably, R' is an alkyl radical of 2 to 10 carbon atoms.

The mol ratio of the barium (salt) to the (organo) lithium compound to form the catalyst complex is from about 0.30:1 to 0.75:1, based on the metals, preferably from about 0.35:1 to 0.60:1, even more preferably about 0.50:1. It is not necessary to preform the catalyst for use in polymerization although such can be done. When the barium salt and organolithium are mixed in toluene, a color change forms quickly indicating complex formation, whereas when benzene is used, color change occurs more slowly. The structures of polybutadiene is essentially the same using a polymerization catalyst complex which has been aged for 1 to 24 hours. However, when the catalyst complex is aged for only 15–30 minutes, the trans-1,4 content of the resulting polymers is raised by about 5 to 7%.

Prior to polymerization the barium salt in hydrocarbon solution and the organo-lithium compound in hydrocarbon solution may be mixed together and the barium compound and lithium compound permitted to complex or react to form the catalyst. The amount of time required to form the complex ranges from a few minutes to an hour or longer depending on the reaction temperature. This should be accomplished under an inert atmosphere and the ingredients may be heated to speed reaction at temperatures of from about 25° to 100° C., preferably from about 40° to 60° C. After the complex has formed, the polymerization solvent and monomer(s) may be added to it or the preformed catalyst dissolved in its solvent may be injected into a reactor containing the monomers dissolved in the hydrocarbon polymerization solvent.

The vinyl monomers to be polymerized with the catalysts of the present invention are those having an activated unsaturated double bond, for example, those monomers where adjacent to the double bond there is a group more electrophilic than hydrogen and which is not easily removed by a strong base. Examples of such monomers are nitriles like acrylonitrile, methacrylonitrile; acrylates and alkacrylates like methyl acrylate, ethyl acrylate, butyl acrylate, ethyl hexyl acrylate, octyl acrylate, methyl methacrylate, ethyl methacrylate, butyl methacrylate, methyl ethacrylate, ethyl ethacrylate, butyl ethacrylate, octyl ethacrylate; the dienes such as butadiene-1,3, isoprene and 2,3-dimethyl butadiene; and the vinyl benzenes like styrene, alpha methyl styrene, p-tertiary butyl styrene, divinyl benzene, methyl vinyl toluene, and para vinyl toluene and the like and mixtures of the same. These monomers can have up to 14 carbon atoms and are free of atoms, radicals and the like which would destroy the catalyst complex. Depending on the monomer employed, the resulting polymers can be rubbery, resinous, or thermoplastic.

Preferred monomers used in the practice of the present invention are butadiene-1,3 and mixtures of butadiene-1,3 and up to about 15% by weight total of the mixtures of styrene and/or isoprene to make rubbery homopolymers and rubbery random copolymers exhibiting crystallinity when stretched in the uncompounded and uncured state, from about 70 to 81% trans 1,4 units, a vinyl content of not over about 12%, a number average molecular weight up to about 300,000 and a broad heterogeneity index ($\overline{M}w/\overline{M}n$ = H.I) of from about 4 to 40. Moreover, by altering the butadiene homopolymer or butadiene-copolymer composition or microstructure a rubber can be prepared which does not crystallize at room temperature but can undergo crystallization on stretching. This behavior closely simulates that of natural rubber. Thus, it is within the scope of this invention to prepare polymers which can serve as replacements in those applications where natural rubber is employed such as in tires. The number-average molecular weight is governed by the ratio of grams of monomer polymerized to moles of carbon-lithium charged. Conversions to polymer in the range of about 90-100% are usually obtained.

Temperatures during solution polymerization can vary from about $-90°$ to $100°$ C. Lower temperatures provide polymers having higher intrinsic viscosities. Preferably polymerization temperatures are from about $-20°$ to $40°$ C. and even more preferably from about $0°$ to $30°$ C. Time for polymerization will be dependent on the temperature, amount of catalyst, type of polymers desired and so forth. Only minor amounts of catalyst complex are necessary to effect polymerization. However, the amount of catalyst employed may vary with the type of polymer desired. For example, when making polymers having a high average molecular weight using a given amount of monomer, only a small amount of the catalyst complex is necessary whereas when making a low average molecular weight polymer, larger amounts of the catalyst complex are employed. Moreover, since the polymer is a living polymer, it will continue to grow as long as monomer is fed to the polymerization system. Thus, the molecular weight can be as high as a million, or even more. On the other hand, very high molecular weight polymers require lengthy polymerization times for a given amount of the catalyst complex, and at lower catalyst concentrations the polymerization rate drops. Moreover, high molecular weight polymers are difficult to handle in the polymerization reactor and on rubber mills and the like. A useful range of catalyst complex to obtain readily processable polymers in practicable times is from about 0.00001 to 0.10, preferably from about 0.00033 to 0.005, mole of catalyst complex computed as lithium per 100 grams total of monomer(s).

Since the polymer in solution in the polymerization media is a living polymer or since the polymerization is a non-terminating polymerization (unless positively terminated by failure to add monomer or by adding a terminating agent such as methanol), block polymers can be prepared by sequential addition of monomers or functional groups can be added. Since the living polymer contains a terminal metal ion, it can be treated with an epoxide like ethylene oxide and then with water to provide a polymer with a terminal hydroxyl group for reaction with a polyisocyanate to jump the polymer through formation of polyurethane linkages.

The polymerization is conducted in a liquid aromatic solvent. While bulk polymerization may be used, such presents heat transfer problems which should be avoided. In solvent polymerizations it is preferred to operate on a basis of not over about 15 to 20% polymer solids concentration in the solvent to enable ready heat transfer and processing. Solvents for the monomers and polymers should not have a very labile carbon-hydrogen bond and which do not act at least substantially as chain terminating agents. They preferably should be aromatic hydrocarbon solvents liquid at room temperature (about $25°$ C.) Examples of such solvents are toluene, the xylenes, the trimethyl benzenes, hemimellitene, pseudocumene, mesitylene, prehnitene, isodurene, O, M, and P cymenes, ethylbenzene, n-propylbenzene, cumene, 1,2,4- or 1,3,5-triethylbenzene, n-butyl benzene and other lower alkyl substituted benzene solvents and the like and mixtures of the same. Toluene is the preferred solvent to use. While other hydrocarbon solvents can be used such as benzene, hexane, heptane, octane, nonane, cyclohexane, cycloheptane, cyclooctane and the like and mixtures of the same, they are not as desirable since they do not give as high trans content. For example, polybutadiences prepared in benzene and paraffinic hydrocarbons have lower trans-1,4 contents with crystalline melting temperatures below $0°$ C. as measured by DTA.

Polymerization, of course, should be conducted in a closed reactor, preferably a pressure reactor, fitted with a stirrer, heating and cooling means, with means to flush with or pump in an inert gas such as nitrogen, neon, argon and so forth in order to polymerize under inert or non-reactive conditions, with means to charge monomer, solvent and catalyst, venting means and with means to recover the resulting polymer and so forth.

After polymerization the catalyst may be terminated by adding water, alcohol or other agent to the polymeric solution. After the polymer has been recovered and dried a suitable antioxidant such as 2,6-di-tert-butyl-p-cresol may be added to the same. However, the antioxidant may be added to the polymeric solution before it is stripped of solvent.

The polymers produced by the method of the present invention can be compounded and cured in the same manner as other plastic and rubbery polymers. For example, they can be mixed with sulfur or sulfur furnishing materials, peroxides, carbon black, $SiO_2$, $TiO_2$, $Sb_2O_3$, red iron oxide, phthalocyanine blue or green, tetramethyl or ethyl thiuram disulfide, benzothiazyl disulfide and the like. Stabilizers, antioxidants, UV light absorbers and other antidegradants can be added to these polymers. They can also be blended with other polymers like natural rubber, butyl rubber, butadiene-styrene-acrylonitrile terpolymers, polychloroprene, SBR, polyurethane elastomers and so forth.

The polymers produced by the method of the present invention can be used in making protective coatings for fabrics, body and engine mounts for automobiles, gaskets, treads and carcasses for tires, belts, hose, shoe soles, and electric wire and cable insulation, and as plasticizers and polymeric fillers for other plastics and rubbers. With large amounts of sulfur hard rubber products can be made.

The following examples will serve to illustrate the present invention with more particularity to those skilled in the art.

EXAMPLE I

PREPARATION OF BARIUM COMPOUNDS

Run 1

To 75.4 milliequivalents of barium metal (5.18g) were added 500 ml of monomethylamine, containing 7.55 milliequivalents of distilled water. The commercial monomethylamine was first distilled from sodium metal dispersion. Upon cooling to $-70°$ C with vigorous stirring, the reaction mixture turned a deep blue color. Approximately 10 percent of the available barium was reacted with water. A solution of anhydrous t-butanol (69.4 milliquivalents) in benzene (3.0 molar) was slowly added to the reactor containing barium, water, and methylamine, The blue color immediately changed to a gray suspension. The product was recovered by flash distillation of monomethylamine to give 10.31 g of a gray-white powder. Approximately 98 percent of the total barium metal was converted to barium salts. A solution of the barium catalyst was prepared by the addition of 680 g of anhydrous toluene. The soluble barium salts comprised 55 percent of the total product. The total alkalinity of a hydrolyzed aliquot of the clear colorless solution measured 0.0572 milliequivalents of hydroxide per gram or 0.8 weight percent barium salts. Additional similar preparations were made in which the amounts of water used were varied, and these runs were designated as Runs 1A, 1B and 1C.

Run 2

This example described the method of preparation of barium t-butoxide in the present of methanol and t-butanol in distilled methylamine. The procedure is similar to Run 1 except that anhydrogen methanol is substituted for water.

To 81.4 milliequivalents of barium metal was added 500 ml of monomethylamine which was flash distilled from sodium. A solution of anhydrous t-butanol (74.2 milliequivalents) and methanol (9.2 milliequivalents) was added to the reactor. The blue solution color immediately changed to a gray suspension. After removal of monomethylamine, 11.58 g of a gray-white powder were obtained. The total alkalinity of the clear, colorless solution in toluene measured 0.104 milliequivalents per gram; 1.45 wt. percent of soluble barium salts.

Run 3

The following procedure describes the preparation of barium t-butoxide in commercial monomethylamine. To 72.8 milliequivalents of barium metal were added 500 ml of commercial monomethylamine, which was withdrawn as a vapor from a cylinder containing the liquefield gas.

The solution color of barium in commercial methylamine was a light grayish-blue. To this solution was added a mixture of anhydrous t-butanol (80.9 milliequivalents) in benzene. A yield of 10.47 g of barium salts was obtained, which represents a quantitative conversion of metal of barium salts of methanol, water and t-butanol, see Table I.

The total alkalinity of a solution of this salt in toluene was found to be 0.088 milliequivalents per gram.

Commercial methylamine, as supplied by Matheson Gas Products, is prepared from methanol and ammonia ["Matheson Gas Data Book," p.192 (1966)]. The assayed purity of the liquid phase is 98.0%. According to the manufacturer, the major impurities present in liquid methylamine are water (0.8%) and di-and tri-methylamines (1.4%) ["Matheson Gas Data Book," p.353 (1966)]; however, it also contains some methanol. When barium is dissolved in commercial methylamine, reaction with methanol and water occurs. Infrared spectra of the barium salts, as a Nujol mull, show strong absorption bands at 1065 $cm^{-1}$ and 3580 $cm^{-1}$ for the carbon-oxygen and oxygen-hydrogen stretching frequencies of the methoxide and hydroxide groups, respectively.

Run 4

The preparation of barium t-butoxide was performed in anhydrous benzene from t-butanol and an excess of barium metal fillings. Tert-butanol (25.03 milliequivalents) was added to a mixture of barium metal (72.5 milliequivalents) in 283 g of benzene. After vigorous stirring for 10 days at 70° C, the yield of barium t-butoxide was calculated as 3.38 g (94 percent), based on the t-butanol content of the recovered product. The total alkalinity of the benzene solution of barium t-butoxide was determined as 0.0114 milliequivalents per gram. An infrared spectrum of a Nujol mull of the product showed only absorptions of the t-butoxide species.

Preparation of the Ba salts of Runs 1–4 was conducted under an argon atmosphere or vacuum. The composition of the soluble barium salts prepared according to Runs 1–4, above, are given in Table 1, below. The total alkalinity was determined by acidometric titration with standard hydrochloric acid (0.1N). The alcohol contents were measured with gas liquid chromatography using the internal standard technique and response factors for the flame ionization detector. The hydroxide ion content was calculated as the difference between the total alkalinity and the total alkoxide contents. The barium metal used in the practice of this invention was 99.5 to 99.7% pure barium (the major impurities were Sr and Ca and the minor impurities were Al, Fe, Mg, Mn, Si, Zn and Na). The barium salts of the present invention may contain up to about 0.5% by weight combined nitrogen (based on total salt including both liquid and solid phases) from the amine solvent, for example, as $(CH_3NH)_2Ba$, which may not be entirely removed at the end of the reaction by distillation, etc after preparation of the catalyst. It will be noted that a complex comprising n-butyl lithium and $Ba(CH_3NH)_2$ containing some free Ba gives a polymer having a microstructure, and similar properties, as shown by polymerization Run No. 10 on page 29 below.

Table I

| | Composition of Barium Salts in Aromatic Hydrocarbon Solutions | | | | | | |
|---|---|---|---|---|---|---|---|
| | Composition of Solution Phase (Milliequivalents per gram of the solution) | | | | Mol % Composition of Ba Salt | | |
| Run No. | Total Alkalinity | t-Butoxide | Methoxide | Hydroxide | t-Butoxide | Methoxide | Hydroxide |
| 1 | 0.057* | 0.052 | — 0 — | 0.005 | 91 | — 0 — | 9 |
| 2 | 0.1045 | 0.0948 | 0.008 | — 0 — | 92 | 8 | — 0 — |
| 3 | 0.0883 | 0.0773 | 0.002 | 0.009 | 88 | 2 | 10 |
| 4 | 0.0114 | 0.0119 | — 0 — | — 0 — | 100 | — 0 — | — 0 — |
| 1A | 0.028 | 0.0273 | — 0 — | 0.0007 | 97.5 | — 0 — | 2.5 |
| 1B | 0.036 | 0.0342 | — 0 — | 0.0018 | 95 | — 0 — | 5.0 |

Table I-continued

Composition of Barium Salts in Aromatic Hydrocarbon Solutions

| | Composition of Solution Phase (Milliequivalents per gram of the solution) | | | Mol % Composition of Ba Salt | | |
|---|---|---|---|---|---|---|
| Run No. | Total Alkalinity | t-Butoxide | Methoxide | Hydroxide | t-Butoxide | Methoxide | Hydroxide |
| 1C | 0.0463** | 0.0363 | — 0 — | 0.010 | 77 | — 0 — | 23.0 |

\* No apparent change in concentration after 3 months.
\*\* After 1 month standing, original value was 0.090.

EXAMPLE II

Butadiene-1,3 polymerizations were conducted in an argon atmosphere in 0.35 l. citrate glass bottles, capped with a butyl rubber gasket. Solvents and monomers were purified by passing the materials through 5 A molecular sieves. n-Butyllithium was obtained from Foote Mineral Co. (1.6N in hexane) and diluted in benzene to a concentration of 0.20 milliequivalents of carbon-lithium per gram. The carbon-lithium content was determined by reduction of vanadium pentoxide [P. F. Collins, C. W. Kamienski D. L. Esmay and R. B. Ellestad, Anal. Chem. 33, 468 (1961)].

In charging the polymerization bottle, the order of addition of materials was solvent first, then n-butyllithium, next the barium salt, all introduced by syringe, and finally the monomer, added by means of a transfer tube. The amount of n-butyllithium charged was sufficient to titrate (scavenge) the acidic impurities present in the solvent and polymerization bottle, plus the calculated amount of initiation of polymerization (see U.S. Pat. No. 3,324,191, col. 2, lines 1–5).

Butadiene (about 20g) was polymerized in toluene (170 ml) at 30° C with about 0.66 millimole of n-butyllithium and about 0.33 millimole of barium salts. The percent conversion and molecular structure of polybutadienes prepared with the barium salts, prepared according to the above Runs and with n-butyllithium alone in the absence of barium salts are given in Table II, below:

tively. The cis-1,4 content was determined from 100% - (% trans-1,4 + % vinyl). Intrinsic viscosities [η] were determined in benzene at 25° C. (0.3 g polymer in 100 ml benzene). All thermal transitions were obtained by DTA (Differential Thermal Analysis) using a heating rate of 20° C/min. commencing at approximately −170° C.

According to the thermal transition measurements, only for polymerizations with n-butyllithium and barium salts which contain the hydroxide anion (Runs 11,13,15 & 16) are polybutadienes formed which have crystalline melting points near room temperature. Initiation of butadiene with n-butyl-lithium and pure barium t-butoxide (Run 14), or barium t-butoxide containing the methoxide ion (Run 12) are not effective for producing crystalline polybutadienes. The molecular structure of polybutadienes prepared with n-butyllithium plus barium salts prepared according to Run 11 and Run 13 are substantially identical. In each case, the barium salt contains the hydroxide ion. The small amount of methoxide (2 mol %) incorporated in the barium salt prepared according to Run 13 apparently does not influence the structure. Polybutadienes prepared with n-butyllithium plus barium t-butoxide with barium hydroxide are very tough, elastic materials which readily form a film. In comparison, the polymers prepared with similar concentration of n-butyllithium in the presence of pure barium t-butoxide or barium t-butoxide and barium methoxide are low viscosity materials. The high molecular weight polybutadienes

Table II

Effect Of The Composition Of The Barium Salt On The Molecular Structure Of Polybutadiene

| Pzn. Run No. | Method of Preparation of Ba Salt Run No. | Mole Ratio $Ba^{2+}/Li^+$(a) | % Conv. (hours) | % Diene Structure | | Peak Crystalline Melting Temp. (° C) | [η] dl gm−1 |
|---|---|---|---|---|---|---|---|
| | | | | Trans | Vinyl | | |
| 10 | — | BuLi only | 100(9) | 55 | 7 | none observed | 0.45 |
| 11 | 1 | 0.45 | 95(27) | 78 | 8 | 29, 35 | 4.20 |
| 12 | 2 | 0.46 | 89(67) | 64 | 9 | −8 | 1.47 |
| 13 | 3 | 0.45 | 84(21) | 73 | 9 | 28, 38 | 4.35 |
| 14 | 4 | 0.49 | 84(21) | 66 | 9 | −4 | 1.32 |
| 15 | 1A | 0.52 | 100(72) | 76 | 7 | 24, 33 | 5.22 |
| 16 | 1B | 0.51 | 100(72) | 76 | 7 | 23, 31 | 6.67 |
| 17 | 1C | 0.47 | 21(66) | 60 | 20 | −24, 46 | not measured, rubber | a the active mole ratio of total barium ion to carbon-lithium ($Ba^{2+}/Li^+$) present for polymerization (does not include carbon-lithium required for titration).

The molar ratio of barium salts to n-butyllithium was based on the total alkalinity of the soluble barium salts and the carbon-lithium concentration measured acording to the oxidimetric method based on vanadium pentoxide, Anal. Chem. 33, 468, 1961, above.

Copolymer composition and percent polybutadiene microstructure were obtained from infrared analysis. The trans-1,4 and vinyl content were determined using the 967 $cm^{-1}$ and 905 $cm^{-1}$ absorption bands, respechave reduced cold flow, probably as a result of their broad molecular weight distribution (as determined by GPC, Gel Permeation Chromatography).

It can be seen from the results of Table I that either hydroxide or methoxide salts are effective in increasing wthe solubility of barium t-butoxide in aromatic solvents. However, it will become apparent from Table II that the hydroxide ion is capable of increasing the trans-1,4 content of polybutadiene to give a high molecular weight, crystalline polymer.

Moreover, while a very minor molar amount of barium methoxide salt (or methoxide salt moiety) less than the hydroxide moiety may be present with the barium t-butoxide-hydroxide salt, it is not too desirable.

It was found that the number-average molecular weight of the polymers prepared with the complex of n-butyl-lithium and the barium salts was equal to the ratio of the weight of polymer formed to the moles of butyllithium. The mole ratio of barium to lithium was based on the moles of total alkalinity of the soluble barium salts (one-half the milliequivalents of titratable base) to the moles of carbon-lithium. The percent conversion was calculated from a measurement of the total solids after removal of solvent and unreacted monomer by flash distillation. Repeating Pzn. Run 12 with a Ba salt made using t-butanol plus t-amyl alcohol instead of methanol (Run 2) gave similar results.

In a polymerization as described in this example using n-butyllithium and a physical mixture of separately prepared Ba(t-butoxide)$_2$ and Ba(OH)$_2$ in the mol ratio of Ba$^{+2}$/Li$^+$ of about 0.5 produced a polybutadiene of low molecular weight and low trans content, see Table IX.

EXAMPLE III

This example demonstrates the usefulness of the barium salts, described in Runs 1 and 3, for the preparation of crystallizable copolymers of butadiene with styrene and isoprene possessing high trans polybutadiene segments with a random comonomer sequence distribution. The polymerization conditions were the same as given in Example II. Styrene and isoprene were charged immediately after the butadiene.

The comonomer sequence distribution of the SBR's prepared according to the present invention is random as determined by NMR measurements; by degradation studies with osmium tetroxide and t-butylhydroperoxide; and by the measurement of glass transition temperature using differential thermal analysis (DTA).

The results obtained are shown in Table III below:

construction of a tire and are characteristic of the high trans polybutadiene rubbers of this invention.

The crystalline melting temperature of the high trans polybutadiene copolymer decreases with increasing comonomer content, according to Flory's equation for melting temperature depression [P. J. Flory, "Principles of Polymer Chemistry," Cornell University Press, Ithaca, N. Y., p. 563 (1953)].

Flory's equation predicts a melting temperature of 17° C for the high trans copolymer with 5% styrene. The melt temperature found by DTA was 13° C. The values of the melt temperature and the intensities of the melt endotherm both decrease with increasing styrene content until at the 25% level of styrene, a melt transition was not observed by DTA.

EXAMPLE IV

A series of runs were carried out over a range of mole ratios of barium salts to n-butyllithium. The polymerization initiator as n-butyllithium and barium salts of t-butanol and water were prepared as described in Run 1. The polymerization charge was the same as given in Example II. The results obtained are shown in Table IV, below:

Table IV

| | Effect Of The Molar Ratio Of Barium Salts To n-Butyllithium On Polybutadiene Microstructure | | | | | |
|---|---|---|---|---|---|---|
| Pzn. Run No. | Catalyst Charge (Millimoles) | | Mole Ratio Ba$^{2+}$/Li$^+$(a) | Conversion % | Diene Structure | |
| | BuLi | Ba Salts | | | %Trans | %Vinyl |
| 30 | 0.76 | 0.0 | 0.0 | 96 | 55 | 7 |
| 31 | 0.72 | 0.17 | 0.24 | 83 | 59 | 10 |
| 32 | 0.66 | 0.26 | 0.39 | 100 | 76 | 7 |
| 33 | 0.72 | 0.33 | 0.46 | 95 | 78 | 8 |
| 34 | 0.64 | 0.34 | 0.54 | 97 | 78 | 7 |
| 35 | 0.61 | 0.41 | 0.68 | 88 | 69 | 9 |
| 36 | 0.63 | 0.47 | 0.75 | 58 | 63 | 12 |
| 37 | 0.70 | 0.67 | 0.96 | 48 | 51* | 32* |

*-Polymer was not soluble in CS$_2$ - Diene structure estimated by IR (Infrared) with cast film.

The results show that the trans/cis ratio increases with an increase in the molar ratio of barium salts to butyl-lithium from 0.0 to 0.5 with little effect on the Table III

| | | Molecular Structure Of Butadiene Copolymers Of Styrene And Isoprene | | | | | | | |
|---|---|---|---|---|---|---|---|---|---|
| Pzn. Run No. | Comonomer | Bound Wt. % Comonomer | g. Total Monomers Per m M n BuLi | Method of Preparation Of Ba Salt Run No. | % Butadiene Microstructure | | Peak Crystalline Melting Temp. (°C) | [η] | Mole Ratio Ba$^{2+}$/Li$^+$ (a) |
| | | | | | Trans | Vinyl | | | |
| 20 | Styrene | 5 | 31.0 | 1 | 76 | 8 | 13 | 3.10 | .48 |
| 21 | Styrene | 15 | 36.2 | 1 | 71 | 8 | −6 | 2.18 | .51 |
| 22 | Styrene | 25 | 73.9 | 3 | 71 | 11 | none observed | 0.68 | .88 |
| 23 | Isoprene | 5 | 32.4 | 3 | 77 | 8 | 34 | 4.40 | .51 |
| 24 | Isoprene | 11 | 36.5 | 1 | 77 | 8 | 3 | 4.72 | .46 |
| 25 | Isoprene | 10 | 38.8 | 1 | 75 | 10 | −1 | 3.16 | .50 |

Table III shows that SBR's containing about 5 percent styrene have crystalline melting temperatures at or slightly below room temperature. Melt temperatures just below room temperature are desirable. Under zero strain, the material is in the amorphous state at room temperature. Upon extension, stress-induced crystallization takes place as the melting temperature of the crystallites is increased. The presence of the crystallites in the strained rubber result in an increase in the green strength of the rubber and an increase in the building tack. Both of these properties are beneficial in the vinyl content. At a ratio above 0.5, the vinyl content increases and the amount of trans-1,4 unsaturation decreases. The effect of mole ratio on microstructure, also, is shown in FIG. 1 in which the curve shows a maximum in trans-1,4 content for a molar ratio of about 0.5 for these runs. The polybutadienes prepared with this ratio are characterized by trans-1,4 contents (weight percent) of about 78%, broad molecular weight distributions, intrinsic viscosities of 5.0 and free of gel.

Figure 2:
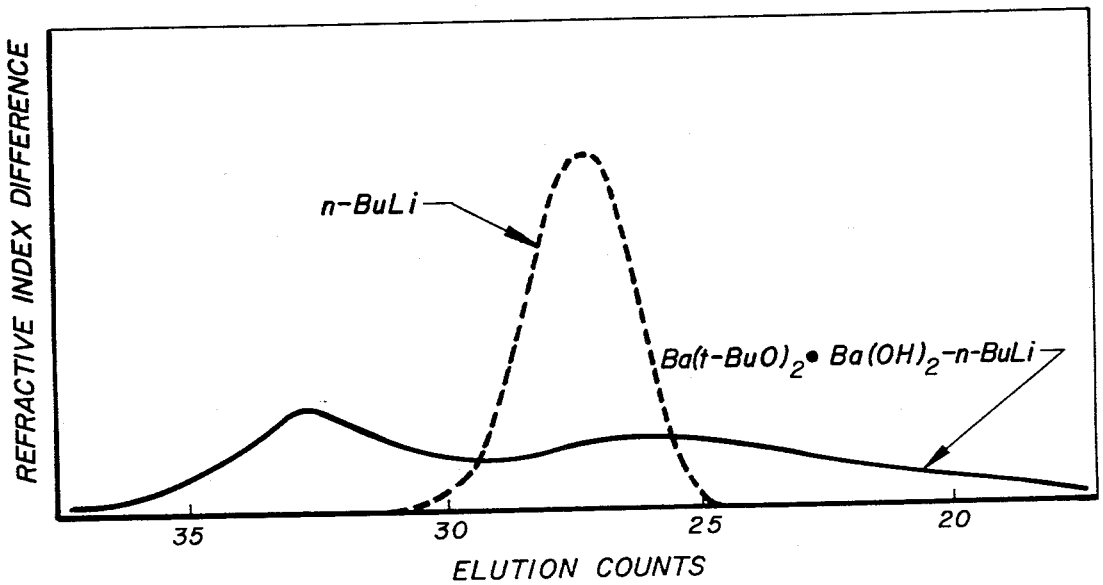
FIG. 2 is a graph showing the gel permeation chromatogram of polybutadienes prepared in toluene using the catalyst of present invention as compared to those prepared from alkyl lithium compound alone.

For example, the solid line of FIG. 2 of the drawings shows the broad molecular weight distribution of the homopolybutadiene of Run 33 above, which had a $\overline{M}_n$ = 41,600, $\overline{M}_w$ = 753,000, a $\overline{M}_w/\overline{M}_n$ = 18.1 and $[\eta]$ = 4.2. On the other hand the dashed line of FIG. 2 of the drawings shows the narrow molecular weight distribution of a homopolybutadiene catalyzed only with n-butyl lithium where $\overline{M}_n$ = 127,000, $\overline{M}_w$ = 147,000, $\overline{M}_w/\overline{M}_n$ = 1.16 and $[\eta]$ = 1.34. The molecular weights were based on polystyrene calibration of GPC. The intrinsic viscosities were done in benzene at 25° C.

The rate of polymerization is less with the butyllithium-barium salt catalyst than with a control polymerization with butyllithium at the same butyllithium concentration. However, quantitative conversions are realized after 16–24 hours at 30° C in toluene. The times can be reduced by elevating the temperature. Mole ratios of $Ba^{2+}/Li^+$ greater than about 0.75 result in polymerizations with conversions generally less than quantitative and in polymers having gel.

EXAMPLE V

Homopolymerizations of isoprene following the general procedure of Example II, above, with the complex of butyllithium and barium salts were carried out, using the barium salts prepared according to Run 3. The homopolymerization rate was decreased by the presence of the barium salt and the 3,4 content was increased. The results are given in Table V below. The percent diene structure was determined by NMR (Nuclear Magnetic Resonance). No measurable amount of 1,2-structure was observed.

Table V

| | | Molecular Structure Of Polyisoprene Prepared With Butyllithium And Barium Salts | | | | | | |
|---|---|---|---|---|---|---|---|---|
| Pzn. Run No. | Initiator Charged (Millimoles) | | Mole Ratio | Wt. Isoprene (Grams) | % Conversion | Diene Structure | | |
| | BuLi | Ba Salts | $Ba^{2+}/Li^+$ (a) | | | % 3,4 | % cis | % trans |
| 40 | 0.61 | — | Control | 17.4 | 100 | 7.4 | 65.5 | 27.1 |
| 41 | 0.61 | 0.46 | 0.75 | 17.9 | 72 | 22.2 | 29.7 | 48.1 |
| 42 | 1.0 | 1.0 | 1.0 | 27.2 | 65 | 53.6 | 10.6 | 35.8 |

Polymerization Runs 40 and 41 were carried out in 105 g of toluene at 30 ° C. while polymerization Run 42 was carried out in 134 g of benzene at 50 °C. In Pzn. Runs 40 and 41 17 grams of isoprene, and in Pzn. Run 42 27 grams of isoprene, were charged to the polymerization bottles.

The net increase in the trans-1,4 content of polyisoprene prepared with the catalyst complex of this invention and compared to n-butyllithium (Table IV) is approximately the same (about 20%) as for polybutadiene alone prepared in a similar fashion. The observed increases were from 54% to 78% for polybutadiene and from 27% to 48% for polyisoprene. Thus, a preference for trans-1,4 addition was observed for both polyisoprene and polybutadiene polymerizations in the presence of the barium salts. However, the microstructure of polyisoprene prepared with n-butyllithium and barium salts was not predominant in trans-1,4 content. As a result, crystalline polyisoprenes were not prepared.

EXAMPLE VI

A physical property relating to polymer crystallization and having special importance for a carcass rubber is green strength. This property has been measured for the high trans butadiene based polymer prepared with n-butyllithium in the presence of barium salts. This polymer has the property of stress-induced crystallization as demonstrated by X-ray diffraction analysis and stress-birefringence measurements.

Green strength data was obtained from stress-strain measurements on unvulcanized polymers with an Instron Tester at room temperature. The crosshead speed was 8.47 mm/sec. Sample specimens were prepared by press molding tensile sheets at 100° C for 5 minutes with a ram force of 13608 kg. The data obtained are shown in Table VI, below:

Table VI

| Polymer | GREEN STRENGTH | | | | | |
|---|---|---|---|---|---|---|
| | A | B | C | D | E | F |
| Mooney Viscosity ML-4 (100° C.) | 54 | 39 | 42 | 72 | 54 | 50 |
| Yield PSI | 128 | 126 | — | — | 22 | — |
| Tensile PSI | 366 | 384 | 197 | 112 | 10 | 34 |
| Elongation at Break, % | 1433 | 2320 | 1338 | 520 | 338 | 80 |

The green strength (uncured and uncompounded polymers) is given in Table VI for the novel polybutadiene and SBR (5% styrene) of this invention as well as for natural, SBR rubber, Alfin SBR and lithium catalyzed polybutadiene for comparison. The green strength of the new butadiene polymers is larger than natural rubber. The green tensile strength of natural rubber is known to be associated with stress crystallization.

The green strength of the new polybutadiene is a result of reinforcement by the crystallites present in the unstretched material and the stress derived from strain-induced crystallization. It is also probable that the high molecular weight chains participate extensively in chain entanglements which contribute to the green tensile strength.

Notes:

A — Polybutadiene of Table II, above, second polymerization using Ba salt of Run No. 1.

B — Butadiene-styrene copolymer (5% Sty) of Table III, above, first polymerization using Ba salt of Run No. 1.

C — Alfin Butadiene-styrene copolymer (5% Sty), Nippon-Alfin Rubber Co., Ltd., Tokyo, Japan, AR-1510. See "Rubber Age," January, 1970, pages 64–71.

D — Natural Rubber (peptized No. 3 ribbed smoked sheets).

E — Solution polymerized polybutadiene, The Firestone Tire & Rubber Co., Diene 55-NF.

F — SBR 1500. Emulsion polymerized copolymer of butadiene-1,3 and styrene, about 23.5% bound styrene.

EXAMPLE VII

The tack strength of the novel high trans SBR (5% styrene) and polybutadiene rubbers of this invention were compared with strain-crystallizing rubbers (natural rubber, high cis-polybutadiene (99% cis-1,4), trans-polypentenamer and Alfin SBR) and with amorphous, non-crystallizing polymers (SBR 1500 and lithium-catalyzed polybutadiene). The measurements were carried out with a Monsanto Tel-Tak instrument with the following operating conditions: contact time (30 sec); contact pressure (0.22 MPa) with a separation rate of 0.424 mm/sec. The test specimens were raw (uncompounded and uncured) polymers pressed between Mylar film at 100° C. and die cut to 5.08 cm × 0.64 cm. The true tack values reported in Table VII represent the difference between the apparent tack (rubber versus rubber) and the value obtained for rubber versus stainless steel.

The results of Table VII show that the tack strength of the high trans SBR is greater than that of non-crystallizing polymers but less than that of the stereo polymers which crystallize on stretching. The tack strength of the high trans SBR rubber is approximately equal to that of Alfin SBR. Alfin rubbers are crystalline at room temperature and they undergo strain-induced crystallization. The lower tack values of Alfin SBR and the high trans SBR relative to natural rubber may be related to the smaller amount of crystallinity produced with strain. The tack strength of the blend of natural rubber and the high trans SBR was intermediate to that of the respective homopolymers.

Table VII

Monsanto Tel-Tak Of Amorphous And Crystallizable Rubbers
Peak

| Polymer Type | H [η]25° C | Crystalline Melting Temperature °C | Tack Strength Apparent Psi | Tack Strength True Psi |
|---|---|---|---|---|
| I | 2.76 | 9 | 38 | 35 (0.24 MPa) |
| II | 3.56 | 28 | 34 | 32 |
| III | 3.65 | −6 | 27 | 15 |
| IV | 2.52 | 42 | 18 | 9 |
| V | 2.50 | 25 | 17 | 7 |
| VI | — | — | 24 | 24 |
| VII | 2.44 | None observed | 13 | 6 |
| VIII | 2.06 | None observed | 22 | 4 |
| IX | — | — | 4 | 3 |

Notes
I. Trans-Polypentenamer Farbenfabriken Bayer AG, TPR.
II. Natural. Same as D. in Table VI.
III. SNAM Progetti's, Italy, Cis-1,4 polybutadiene (99% cis).
IV. Alfin. Same as C. in Table VI.
V. High trans SBR. Same as B. in Table VI.
VI. 50/50 by weight blend of natural and high trans SBR, II and V, above.
VII. Firestone Tire & Rubber Co. 's solution polybutadiene. Same as E. in Table VI.
VIII. SBR 1500. Same as F. in Table VI.
IX. Polybutadiene. Same as A. in Table VI.

Table VIII

| Pzn. Run No. | Pzn. of Ba Compound | Mole Ratio Ba²⁺/Li⁺(a) | Pzn. Solvent | Pzn. Temp. °C. | Pzn. Time, Mins. | Yield, % | Microstructure of Diene Units Trans | Vinyl | Cis | [θ] |
|---|---|---|---|---|---|---|---|---|---|---|
| — | Di(tert-butoxy) barium. Prep. unknown. See U.S. Pat. 3,629,213, Ex. 18 | 0.5 | Toluene | 80 | 60 | 88.3 | 62.3 | 9.5 | 28.2 | not reported |
| 50 | Pure Ba(t-BuO)₂*ᴹ | 0.5 | Toluene | 80 | 60 | 86.8 | 57.6 | 10.5 | 31.9 | 0.45 |
| 51 | Pure Ba(t-BuO)₂ᴺ | 0.48 | Toluene | 30 | 42 hrs | 51.0 | 57 | 10 | 33 | medium viscosity oil |
| 52 | Pure Ba(t-BuO)₂, Table I, Run No. 4 (Table II, Pzn. Run No. 14). (prepared in benzene), above | 0.49 | Toluene | 30 | 21 hrs | 84 | 66 | 9 | 25 | 1.32 |
| 53 | Ba(t-BuO)₂ containing methoxide and hydroxide, Table I, Run No. 3, above | 0.5 | Toluene | 50 | 17 hrs | 96 | 71 | 9 | 20 | 1.12 |
| 54 | Ba(t-Buo)₂-hydroxide Table I, Run No. 1 (Table II, Pzn Run No. 11), above * 20g. Bd/0.9m M n BuLi | 0.45 | Toluene | 30 | 27 hrs | 95 | 78 | 8 | 14 | 4.20 |

Notes:
ᴹPrepared by reaction of barium metal and tert-butanol in liquid NH₃ free of H₂O and amines. NH₃ distilled off and replaced with hydrocarbon solvent before use in polymerization.
ᴺMonomethyl amine was flash distilled from sodium ribbon. To the pure condensed amine was added barium and tertiary butanol which were allowed to react. The amine was distilled from the barium di(tertiary butoxide) which was slurried in benzene. The clear portion of the benzene solution of the Ba(t-BuO)₂ was used as the catalyst - the total alkalinity was 0.0127 and the composition of the barium salt was 100% t-butoxide.

These results show that pure barium di(tert-butoxide) does not give the improved results obtained by using the salts of the present invention.

EXAMPLE IX

The method for the polymerization of butadiene using n-butyllithium and a barium compound in toluene at 30° C. of this example was the same as that of Example II, above, except as shown in Table IX, below:

Table IX

| Pzn. Run No. | Preparation of Ba Compound | Mole Ratio Ba²⁺/Li⁺(a) | Pzn. Time, Hrs. | Yield (Conv.), % | Microstructure of Diene Units Trans | Vinyl | Cis | Peak Cyst. Melt. Temp., °C. | [η] |
|---|---|---|---|---|---|---|---|---|---|
| 60 | Ba(t-BuO)₂-hydroxide Table I, Run No. 1 (Table II, Pzn. Run No. 11) above | 0.45 | 27 | 95 | 78 | 8 | 14 | 29, 35 | 4.20 |
| 61 | Physical mixture of Ba(t-BuO)₂ and | 0.60 | 22 | 82 | 63 | 8 | 29 | −19 | 0.83 |

Table IX-continued

| Pzn. Run No. | Preparation of Ba Compound | Mole Ratio Ba$^{2+}$/Li$^+$(a) | Pzn. Time, Hrs. | Yield (Conv.), % | Microstructure of Diene Units | | | Peak Cyst. Melt. Temp., °C | [η] |
|---|---|---|---|---|---|---|---|---|---|
| | | | | | Trans | Vinyl | Cis | | |
| 62 | Ba(OH)$_2$$^u$ Ba(t-BuO)$_2$ + 10% H$_2$O$^r$ | 0.51 | 26 | 87 | 62 | 9 | 29 | −19 | 0.68 |

Notes:
$^u$Barium di(tert-butoxide) was prepared as in M in Example VIII, above. Ba(OH)$_2$ was prepared in the same way but H$_2$O was substituted for the t-butanol. A mixture of the two compounds was then made and used in the polymerization run.
$^r$Barium di(t-butoxide) was prepared in the same way as shown for M of Example VIII, above. The water for reaction with the Ba(t-BuO)$_2$ was added as a mixture with the polymerization solvent (toluene).

Table X

| Pzn. Run No. | Ba Compound | Mole Ratio Ba$^{++}$/Li$^+$(a) | Pzn. Temp. °C | Pzn. Time, Hrs. | Yield % | Wt. % Sty. | | Sty. place-ments | Microstructure of Diene Units | | |
|---|---|---|---|---|---|---|---|---|---|---|---|
| | | | | | | Charged | Incorp. | | Trans | Vinyl | Cis |
| 70 | Barium stearate U.S. Patent No. 3,629,213, Ex. 13 (as reported) | 0.5 | 80 | 20 | 94.6 | 25 | 22.7 | $a$ | 70.5 | 7.8 | 21.7 |
| 71 | Barium distearate, ACS Reagent Grade | 0.5 | 50 | 4 | 96 | 24 | 26 | $R$ | 56.2 | 13.4 | 30.4 |

Note:
$^a$Presumed random placement because reported 0% recovery of oxidative degradation product (column 12, lines 53–54 and column 10, lines 1–6).
$^R$Block. Determined by sampling during conversion - % polymer solids and monomers as a function of elapsed polymerization time. Styrene mostly polymerized during 60–96% conversion range. Charge ratio: 25 grams total monomers/1m mole n-butyllithium.

EXAMPLE XI

A barium salt was prepared in a manner similar to Example I, Run 1, above, except that it contained 5 mol % hydroxide. The total alkalinity of the barium salt solution phase was 0.057 meg./g. solution. The barium salt and n-butyllithium solutions were (I) mixed and aged at room temperature for 30 minutes and also were (II) mixed and aged at 50° C. for 30 minutes. In each of (I) and (II) the mole ratio of Ba$^{2+}$/Li$^+$(a) was 0.5. Polymerizations of butadiene in benzene at 30° C. were then conducted following the procedure of Example II, above. The results obtained are shown below in Table XI:

Table XI

| Pzn. Run No. | % Conv. (Hours) | Diene Microstructure | | | Peak Cryst. Melt. Temp., °C | [η] |
|---|---|---|---|---|---|---|
| | | Trans | Vinyl | Cis | | |
| 80(I) | 93(44) | 70 | 8 | 22 | −16 | 1.43 |
| 81(II) | 88(44) | 68 | 8 | 24 | −16 | 1.50 |

In both cases the polybutadienes obtained were amorphous at about 25° C. The results show the difference obtained when benzene is used as a solvent during polymerization as compared to toluene.

EXAMPLE XII

The procedure of Example 1, Run 1 was repeated except that liquid NH$_3$ was used in place of monomethyl amine. The mol ratio of H$_2$O to t-butanol was 5:95. The resulting barium salt solution had a total alkalinity of 0.062 meq./g. solution, t-butoxide of 0.059 meq./g. solution, and hydroxide of 0.003 meq./g. solution. The barium salt solution was then mixed with the n-butyllithium solution to provide a Ba$^{2+}$/Li$^+$(a) mole ratio of about 0.5. The mixed catalyst solution was then used to polymerize butadiene in toluene at 30° C. for 42 hours (93% conversion) following the procedure of Example II, above, to provide a polybutadiene having a trans content of 72%, vinyl content of 8%, cis content of 20%, an intrinsic viscosity in benzene at 25° C. of 2.31, and crystalline melting temperature of 22° C; 37° C.

EXAMPLE XIII

A barium salt was prepared according to the method of Example I, Run 1, above, except that only 5 mol % of H$_2$O was used; it had a total alkalinity of 0.04 meq./g. of solution. Using this barium salt and n-butyl lithium, mole ratio of Ra$^{++}$/Li$^+$(a) of about 0.5, butadiene was polymerized in toluene following the procedure of Example II, Run 11, above. The results obtained are shown in Table XII, below.

Table XII

| Pzn. Run No. | Pzn. Temp. °C | Conv. % (Hrs.) | Microstructure | | | Peak Cryst. Melt. Temp. °C | Tg, °C | [η] |
|---|---|---|---|---|---|---|---|---|
| | | | Trans | Vinyl | Cis | | | |
| 90 | 15 | 98(24) | 80.4 | 7 | 12.6 | 19,32 | −91 | 5.90 |
| 91 | 5 | 90(144) | 77 | 6 | 17 | 29,37 | −93 | 7.02 |

This data shown the higher viscosities obtained at lower polymerization temperatures. The resulting homopolybutadienes were crystalline near room temperature. Tg = glass transition temperature.

EXAMPLE XIV

A barium salt was prepared according to the method of Example I, Run 1, above. It was used to prepare two polybutadienes according to the method of Example II, Run 11, above using a $Ba^{++}/Li^+(a)$ mole ratio of about 0.5. One homopolybutadiene had an overall trans content of 74%, a vinyl content of 8%, a cis content of 18%, and an intrinsic viscosity of 5.1. The second homopolybutadiene had an overall trans content of 75%, a vinyl content of 8%, a cis content of 17% and an intrinsic viscosity of 4.66. Sixty parts by weight of the first polybutadiene were blended with 40 parts by weight of the second polybutadiene to provide a polybutadiene blend with an average intrinsic viscosity of 4.9. One hundred parts by weight of the polybutadiene blend were then compounded (mixed) with 0.5 part of stearic acid, 1 part of zinc oxide, 1 part of "Santocure" (Monsanto Chem. Co., N-cyclohexyl-2-benzothiazole sulfenamide), and 1 part of sulfur. Samples of the compounded polybutadiene blend were cured at 300° F. for 20 minutes (best cure). Samples of the cured gum (no reinforcing agent) rubber polybutadienes were then subjected to x-ray analysis at room temperature. The gum rubber vulcanizates of the polybutadiene show x-ray diffraction patterns characteristic of crystalline trans-1,4 polybutadienes in the unstretched state as shown in FIG. 3, picture a (the outer light ring or band) of the drawings. Upon elongation at 100% picture b, at 200% picture c and at 300% picture d, the diffraction patterns show the fiber pattern indicative of oriented crystalline regions of the polymer; they show the diffraction rings associated with the (100) plane of the trans-1,4 polybutadiene crystallites [Lincei-Rend. Sc. Fis. Mat. e Nat.—Vol. XX—Gingno p. 729 (1956)].

EXAMPLE XV

One hundred parts by weight of the SBR containing 5% styrene, the copolymer of Run 20 of Example III, above, was compounded with 1 part of stearic acid, 3 parts of zinc oxide, 1 part of "Santocure" and 1 part of sulfur. Samples of the compounded copolymer were then cured at 300° F. for 30 minutes (best cure). The cured samples were then x-rayed at room temperature.

In the unstretched state, this 5% styrene SBR has an x-ray diffraction pattern representative of an amorphous material, FIG. 4, picture $a'$ of the drawings. FIG. 4, also, shows the crystalline x-ray diffraction patterns for this copolymer when stretched at elongations of 225% picture $b'$, of 400% picture $c'$ and of 500% picture $d'$. Above 200% elongation, a decrease in the intensity of the amorphous halo occurs concurrent with the appearance of x-ray reflexions as equitorial arcs indicating the formation of crystallites oriented parallel to the stretching direction.

Stress-optical measurements have shown that gum rubber vulcanizates of high trans SBR's (5% styrene) of the present invention undergo stress-induced crystallization at room temperature although they are amorphous in the unstretched state at room temperature. At low extents of elongation, no increase in stress-optical coefficient (ratio of birefringence to stress during the relaxation process) as a function of time is observed; however, an increase in stress-optical coefficient was observed for elongations greater than 200%. In stress-relaxation experiments, the ratio of birefringence to stress increases with time for an amorphous rubber that crystallizes during the course of the stress-relaxation tests ["The Physics of Rubber Elasticity," L. R. G. Treloar, Oxford at the Clarendon Press, Gt. Brit., 2nd. Ed., 1958, Chapter 10, pages 197–234]. Thus, these results demonstrate that the present high trans rubbers are stress crystallizing rubbers. Building tack and green strength are related to the crystallizability of a rubber and it has been demonstrated above that this set of properties is exhibited by the polymers of this invention.

EXAMPLE XVI

Styrene was polymerized in toluene following the general method set forth in Example II, above. The polymerization conditions and results obtained are shown below in Table XIII:

Table XIII

| Pzn. Run No. | Method of Prep. of Ba Salt | Mole Ratio $Ba^{++}/Li^+(a)$ | Pzn. Temp. ° C. | % Conv. (hours) | [η] | Estimated Mn by G P C |
|---|---|---|---|---|---|---|
| 100 | Ex. I, Run 1 | 0.49 | −20 | 100(20) | 0.464 | 47,000 |
| 101 | Ex. I, Run 3 | 0.75 | 30 | 100(½) | 0.420 | not measured |

Run 100, charge ratio 20.5g. Sty/0.74 m mole n-butyl-lithium.
Run 101, charge ratio 21.8g. Sty/0.49 m mole n-butyl-lithium.

The heterogeneity index $\overline{Ms}/\overline{Mn}$ of the homopolystyrene of Pzn. Run No. 100 was 2.0. Using the catalyst system of the present invention, 100% conversion of styrene to polystyrene in toluene is obtained in 30 minutes at 30° C. On the other hand, with butadiene 5% conversion to polymer in toluene is obtained in 30 minutes at 30° C. while 100% conversion is obtained in 24 hours at 30° C.

EXAMPLE XVII

Butadiene-styrene copolymers were prepared according to Example III, Pzn. Run 20, above. The tack strength of the resulting copolymers were tested according to Example VII, above, in the raw, uncured state and in the compounded, uncured state. The results obtained are shown in Table XIV, below:

Table XIV

| Pzn. Run No. | Wt. % Bound Styrene | [η] | % Diene Microstructure Trans | % Diene Microstructure Vinyl | Peak Cryst. Melt Temp., ° C | Tack Strength Apparent PSI | Tack Strength True PSI | Tack Strength True MPa |
|---|---|---|---|---|---|---|---|---|
| 110 | 9.4 | 4.24 | 76.5 | 6.9 | −4,29.5 | 31.2ʳ | 28.2 | 0.19 |
| 111 | 14.7 | 3.85 | 77.7 | 7.1 | −6.5ˢ | 26.5ʳ | 24.7 | 0.17 |
| 112 | 5.0 | 6.25 | 79.2 | 6.7 | 6.5,32.1 | 16.2ʳ | 16.2 | 0.11 |
| 113 | 13.7 | 3.10 | 74.5 | 7.4 | −6.5ˢ | 24.3ᶜ | 17.9 | 0.12 |
| 114 | Natural | 3.56 | | | | | | |

Table XIV-continued

| | | | | | |
|---|---|---|---|---|---|
| Rubber [D] | — | — | 28 | 31.0[E] | 25.9 | 0.18 |

Notes:
[D]Same as in Example VI, above.
[E]Single melt endotherm.
[F]On raw polymer.
[G]Polymer first compounded with the following ingredients:

| Parts by Weight | Material |
|---|---|
| 100 | Polymer |
| 20 | HAF-HS Carbon black |
| 20 | FEF Carbon Black |
| 5 | "Philrich" No. 5 oil, highly aromatic oil, Phillips Chem. Co. |
| 2 | Stearic acid |
| 1 | Sulfur |
| 3 | Zinc Oxide |
| 1 | "Santocure" |
| 2 | "AgeRite Superflex," a diphenyl-amine-acetone reaction product, antioxidant, R. T. Vanderbilt Co., Inc. |

EXAMPLE XVIII

A barium salt was prepared according to the method of Example I, Run 1 above except that the mol ratio of $H_2O$ to tert-butanol was 5:95. Butadiene was then polymerized in toluene at 15° C. using, according to the general method of Example II, above, some other butyl lithium compounds. The other polymerization conditions and the results obtained are shown in Table XV, below:

Table XV

| Pzn. Run No. | Type of BuLi (m Moles) | Bdn. (g.) | % Conv. (hrs.) | Mole Ratio $Ba^{++}$ $Li^+$(a) | % Butadiene Microstructure | | $[\eta]$ | Peak Cryst. Melt Temp., ° C. |
|---|---|---|---|---|---|---|---|---|
| | | | | | Trans | Vinyl | | |
| 120 | Normal (0.72) | 24.8 | 97 (113, over the weekend) | 0.52 | 80.4 | 6.8 | 5.90 | 32,42 |
| 121 | Secondary (0.71) | 21.5 | 100 (41) | 0.53 | 78.7 | 6.2 | 7.39 | 34,42 |
| 122 | Tertiary (0.72) | 24.2 | 100 (41) | 0.52 | 80.0 | 6.5 | 6.09 | 32,42 |

Table XVI

| Instron Tester Crosshead Speed | Natural | | High Trans SBR | |
|---|---|---|---|---|
| | 1 in./min. | 20 in./min. | 1 in./min. | 20 in./min. |
| Green Tensile, psi | 380 | 745 | 419 | 652 |
| MPa | 2.62 | 5.14 | 2.89 | 4.50 |
| Elongation at break, % | 792 | 832 | 1535 | 1821 |

EXAMPLE XIX

The green (uncured) strength of a compounded high trans SBR copolymer of the present invention was compared with that of compounded natural rubber. The SBR copolymer was the same as that shown in Example III, Run 20, above. The natural rubber (D) was the same as that shown in Example VI, above. 100 parts by weight of each polymer were compounded with 20 parts of HAF-HS carbon black, 20 parts of FEF carbon black, 3 parts of zinc oxide, 2 parts of stearic acid, 1.2 parts of "Age Rite Spar" (a mixture of mono-, -, di-, and tri-styrenated phenols, antioxidant, R. T. Vanderbilt Co., Inc.), 1.2 parts of "Santocure," and 2.25 parts of "Crystex" (refined sulfur, about 90% insoluble, Stauffer Chemical Co.). After compounding, the compounded but uncured rubber stocks were tested, and the results obtained are shown in Table XVI, below:

SBR 1712 cold emulsion copolymerized butadiene- and styrene (about 23.5% bound styrene) when compounded and tested at a standard crosshead speed of 20 in./min. shows a green tensile strength of 49.3 psi or 0.34 MPa ("Rubber Age," April, 1974, page 52).

The embodiments of the invention in which an exclusive property or privilege is claimed are defined as follows:

1. A compound having the formula

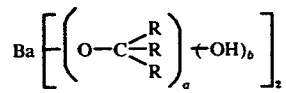

where at least one R is a methyl or cyclohexyl radical and where the remaining Rs are selected from the group consisting of alkyl and cycloalkyl radicals having from 1 to 6 carbon atoms which may be the same or different, and where the mol ratio of a to b is from about 99.5:0.5 to 88:12.

2. A compound according to claim 1 where the mol ratio of a to b is from about 97.5:2.5 to 90:10.

3. A compound according to claim 2 where the Rs are methyl radicals.

4. A compound according to claim 1 dissolved in an aromatic hydrocarbon solvent.

5. A compound according to claim 4 in which said aromatic hydrocarbon solvent does not have a very labile carbon-hydrogen bond and which does not act at least substantially as a chain terminating agent.

6. The method for making a compound having the formula

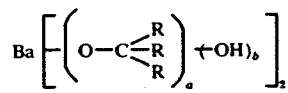

where at least one R is a methyl or cyclohexyl radical and where the remaining Rs are selected from the group consisting of alkyl and cycloalkyl radicals having from 1 to 6 carbon atoms which may be the same or different, and where the mol ratio of a to b is from about 99.5:0.5 to 88:12 which comprises under an inert atmosphere reacting barium metal in liquid $NH_3$ or amine solvent for said barium with a tertiary carbinol having the formula

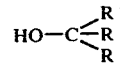

where R is the same as defined about and $H_2O$, the mol ratio of said carbinol to $H_2O$ being from about 99.5:0.5 to 88:12, the temperature during reaction being from about $-100°$ C. up to the boiling point of the solvent, said amine being selected from the group consisting of saturated non-chelating non-polymerizable aliphatic, cycloaliphatic and heterocyclic primary and secondary monoamines and polyamines and mixtures of the same having from 1 to 12 carbon atoms and from 1 to 3 nitrogen atoms, and removing said compound from said $NH_3$ or amine solvent and any excess carbonol at the end of the reaction.

7. The methods according to claim 6 where the mol ratio of a to b is from about 97.5:2.5 to 90:10.

8. The method according to claim 7 where the Rs are methyl radicals.

9. The method according to claim 6 containing the subsequent and additional step of dissolving said compound in an aromatic hydrocarbon solvent.

10. The method according to claim 9 in which said aromatic hydrocarbon solvent does not have a very labile carbon-hydrogen bond and which does not act at least substantially as a chain terminating agent.

* * * * *

UNITED STATES PATENT AND TRADEMARK OFFICE
CERTIFICATE OF CORRECTION

PATENT NO. : 4,020,115
DATED : April 26, 1977
INVENTOR(S) : Ivan Glen Hargis, Russell Anthony Livigni, Sundar Lal Aggarwal It is certified that error appears in the above-identified patent and that said Letters Patent are hereby corrected as shown below:

Claim 6, column 28, line 8, which reads: "about" should read ---above---.

Claim 6, column 28, line 18, which reads: "carbonol" should read ---carbinol---.

Signed and Sealed this

Twenty-eighth Day of June 1977

[SEAL]

Attest:

RUTH C. MASON
Attesting Officer

C. MARSHALL DANN
Commissioner of Patents and Trademarks